United States Patent [19]

Murtagh

[11] Patent Number: 5,333,330
[45] Date of Patent: Aug. 2, 1994

[54] FEMININE URINARY DEVICE

[76] Inventor: Daniel S. Murtagh, 433 Brookside Dr., Toledo, Ohio 43615

[21] Appl. No.: 940,533

[22] Filed: Sep. 4, 1992

[51] Int. Cl.$^5$ ............................................. A47K 11/00
[52] U.S. Cl. ...................................... 4/144.3; 4/144.2
[58] Field of Search .................... 4/144.4, 141.1, 144.2; 141/337, 338

[56] References Cited

U.S. PATENT DOCUMENTS

| | | | |
|---|---|---|---|
| 2,490,969 | 12/1949 | Kinyon | 128/350 |
| 4,023,216 | 5/1977 | Li | 4/144.3 |
| 4,681,573 | 7/1987 | McGovern et al. | 604/329 |
| 4,751,751 | 7/1988 | Reno | 4/144.4 |

Primary Examiner—Henry J. Recla
Assistant Examiner—Greg Vidovich
Attorney, Agent, or Firm—Marshall & Melhorn

[57] ABSTRACT

A urinary device to permit a user to urinate from an upright position, and providing more accurate discharge of the urine. The urinary device includes a funnel-shaped element placed around the urethra of the user. The urine is directed through an aperture into a tubular element. In one embodiment, the funnel-shaped and tubular elements are formed from a pair of opposed planar side walls hinged at the anterior and posterior longitudinal edges, with the device packaged in a flat-folded condition. In another embodiment, the tubular element is provided with accordion pleats extending the full length of the tubular element. The accordion pleats may be compacted for packaging purposes and then extended at time of use.

5 Claims, 2 Drawing Sheets

FEMININE URINARY DEVICE

BACKGROUND OF THE INVENTION

1. Field of the Invention

This invention relates to a urinary device, and more particularly to an improved disposable feminine urinary device which permits a female to urinate comfortably and hygienically from a standing position and to more accurately direct the stream of urine as the urine exits the device.

2. Description of the Prior Art

For sanitary and medical reasons, as well as reasons of convenience, it is desirable to enable a woman to urinate from a standing position. Women are concerned about the dangers (real or imagined) of contracting a disease from contact with a public toilet seat. In addition, women participate in activities where toilet facilities are either non-existent, such as hunting or flying, or may be overcrowded, such as sporting events or concerts.

These are problems longstanding in the art, and numerous devices have been proposed. U.S. Pat. No. 4,937,890 describes a flat-folded urinary aid which has a flat-folded tubular element and a flat-folded funnel-shaped element. The two side walls of the tubular element are creased or scored between their longitudinal edges. The side walls of the funnel-shaped element are scored along a pair of lines extending from the juncture of the funnel-shaped element with the tubular element to intersect at a point approximately one-half the length of the funnel-shaped element. The funnel-shaped element may be expanded into a substantially elliptical shaped opening and the tubular element expanded to form a tube coaxial with the funnel-shaped element by compressing the top and bottom longitudinal edges toward each other.

U.S. Pat. No. 5,091,998 discloses a funnel device which includes a funnel for confining urine and a tube for directing the urine from the outlet of the funnel. The rim on the inlet of the funnel is semi-rigid. The wall of the funnel is sufficiently flexible to be folded against the rim for storage. The tube is provided with at least one corrugated area where the tube may be bent to store the tube, or to direct the flow of urine. The tube may be attached to the outside of the funnel, or may extend through the funnel outlet into the funnel. If the tube extends into the funnel, the tube is cut away so that the tube is opened lengthwise to lie flat against and affixed to the wall of the funnel.

U.S. Pat. No. 4,756,029 discloses a flat, flexible pad having a hingedly attached flap with expandable side walls to permit the flap to move to an open expanded position forming a conduit for the passage of urine.

U.S. Pat. No. 4,734,941 discloses a urine conducting appliance which includes a flexible layered sheet adapted to be folded in a U-shape to fit between the legs of a female and direct urine to a receptacle. The flushable appliance provides for rapid disintegration of structural integrity when in contact with water.

The oblique, conical-like urinary device shown in U.S. Pat. No. 4,681,573 includes a flat blank which may be curved, creased or folded into the desired shape. U.S. Pat. No. 4,608,046 discloses a urinary device in the form of a flat folded tubular member which expands when the fold lines are squeezed together.

The device for urine specimen collection shown in U.S. Pat. No. 3,572,318 is made from a foldable sheet of material which forms into a funnel. The device includes a stabilizer flap for attaching and positioning the device in the mouth of a container during the taking of a specimen.

Many of the devices proposed in the prior art are complex devices which are difficult to set up and awkward to use. In many cases, two hands are required to use the device, which makes it difficult to hold a specimen container or to hold away clothing that might obstruct positioning of the device. In other cases the outlet of the device may be difficult to see, complicating directional control. Some devices are bulky and difficult to store. Additionally, many of the devices are relatively expensive to manufacture and are not readily disposable after use. It is apparent that no device encompasses the desirable features of low cost of manufacture, ease of storage, ease of use, and ease of disposal. Therefore, those in the art continue to seek a solution to these problems.

SUMMARY OF THE INVENTION

In order to solve these problems, a novel feminine urinary device is provided. The device is formed from a light weight sheet material and can be folded flat during storage and transit. The device may be unfolded and readily formed into shape for use. It has a forwardly projecting outlet from which voided urine may be easily directed. The device is readily disposable.

The urinary device includes a flat-folded funnel element expandable to a funnel shape having a discharge portion, a top edge defining an inlet, and a pair of opposed planar walls. The walls are hingedly joined along a linear posterior edge and a linear anterior edge. The posterior and anterior edges converge toward each other from the inlet to the discharge portion.

The device also includes an elongate flat-folded tubular element extending outwardly from the discharge portion of the funnel element and terminating in an outlet. The flat-folded tubular element includes a pair of opposed planar walls, each wall being coplanar with and joined to a respective one of the walls of the funnel element.

A second embodiment of the invention consists of a funnel body tapered from an inlet to an outlet, and a tubular element extending through the outlet and provided with a flange secured to the inner surface of the funnel body. The tubular element is provided with pleats so as to be extensible and flexible.

An object of the present invention is to provide a urinary device for females which is compact, easy to carry, and disposable.

Another object of the invention is to provide a urinary device for females which can be comfortably used by a female, and incorporating features designed to facilitate the directing of voided urine in a desired direction.

It is yet another object of the invention to provide a urinary device which may be easily and inexpensively manufactured.

An additional object of the invention is to provide a urinary device which can be packaged in a sterile condition, used to facilitate collection of urine samples, and disposed of.

BRIEF DESCRIPTION OF THE DRAWINGS

The above, as well as other objects and advantages of the present invention, will become readily apparent to those skilled in the art from the following detailed description of a preferred embodiment when considered in the light of the accompanying drawings in which.

DESCRIPTION OF THE PREFERRED EMBODIMENT

Figure 1:
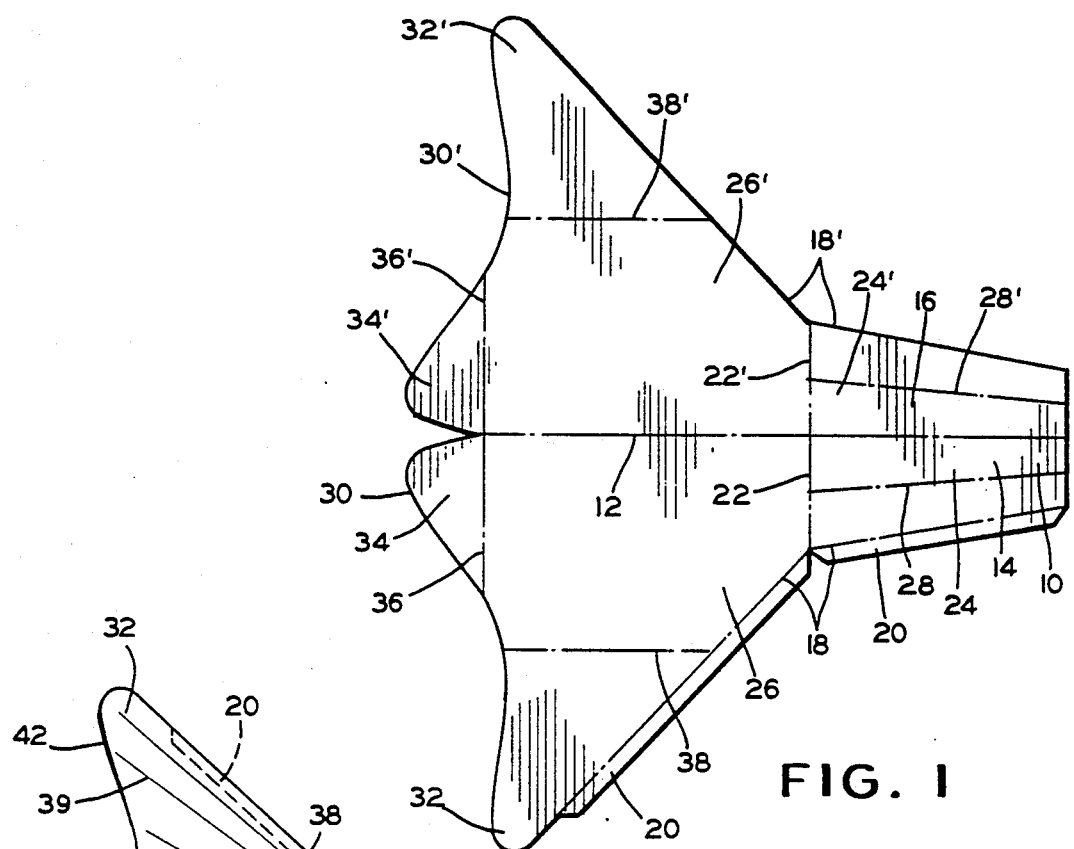
FIG. 1 is a plan view of a blank from which a urinary device of the present invention may be formed.

The urinary device of the present invention may be constructed from any suitable material, such as paper or light-weight cardboard. The urinary device may advantageously be formed from a single blank 10. As illustrated in FIG. 1, the blank 10 is provided with a scored centerline, indicated by a phantom line 12, dividing the blank 10 into two halves 14 and 16 generally symmetric about the centerline 12. Each half 14 and 16 is provided with an edge, 18 and 18' respectively, opposite the line 12. The edge 18 is suitably provided with tabs 20, flexible along a scored line on the edge 18 as indicated in phantom line. Except for the tabs 20, the two halves 14 and 16 are substantially identical in structure. Accordingly, only the elements of the half 14 will be described. The corresponding elements of the half 16 are indicated in prime numbers.

A line 22, extending perpendicularly to the line divides the half 14 into two portions, 24 and 26. The portion 24 is scored along a line 28 extending longitudinally the length of the portion 24, substantially midway between the line 12 and the edge 18.

The portion 26 has an undulate edge 30 extending generally perpendicularly to the line 12 and forming a corner 32 at the edge 18. A flap 34 is formed by the edge 30 and a scored line 36. The portion 26 is further scored along a line 38, formed substantially parallel to the line 12 and located substantially midway between the line 12 and the corner 32.

The edge 18 is divided into two linear segments by the line 22, one segment in each of the portions 24 and 26. The edge 18 of the portion 24 converges toward the line 12 less sharply than does the edge 18 of the portion 26. Thus, the edge 18 forms an oblique angle at the point of intersection with the line 22.

Figure 2:
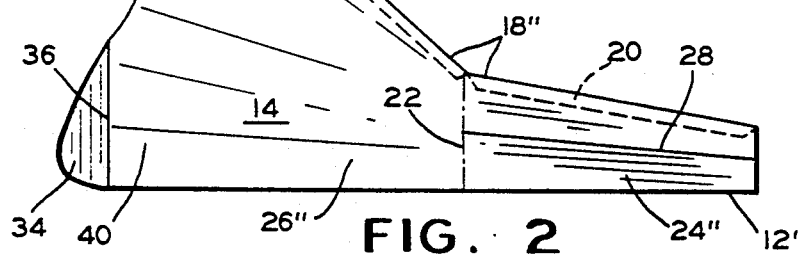
FIG. 2 is a side elevational view of the urinary device formed from the blank shown in FIG. 1.

The blank 10 may be folded flat along the centerline 12 to form a pair of opposed halves or side walls 14 and 16, respectively, of the urinary device. As illustrated in FIG. 2, in the finished device the centerline 12 will thus form a posterior edge 12' at the fold. If a single blank 10 is not used to form the urinary device, the device may be formed from two blanks (not shown), cut in the shape of the side walls 14 and 16, and scored with the lines hereinbefore described.

The side walls 14 and 16 are hinged together along the length of an anterior edge 18", formed by joining the edges 18 and 18'. The edges 18 and 18' may be joined by folding the tabs 20 over the edge 18' of the side wall 16 and attaching the tabs 20 by suitable adhesive means to the side wall 16. Alternatively, the edges 18 and 18' may be joined by a suitable adhesive material. It will be understood that if the urinary device is formed from two sheets of material, a similar arrangement of tabs (not shown) or adhesive material may be used to flexibly join the posterior edge 12'.

Figure 3:
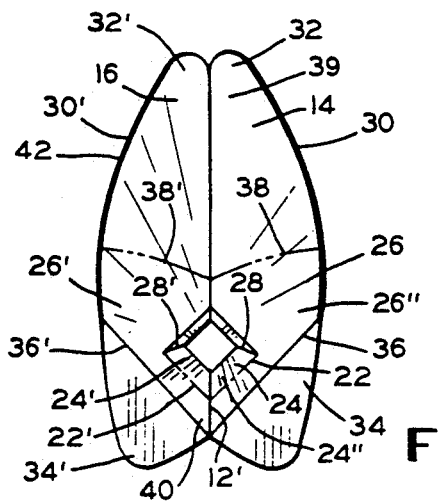
FIG. 3 is a plan view of the urinary device shown in FIG. 2, showing the interior of the funnel and tubular elements.

As shown in FIGS. 2 and 3, the device has a tubular element 24", formed from the portions 24 and 24' and a funnel element 26", formed from the portions 26 and 26'. The posterior edge 12' of the urinary device is straight along its length. The anterior edge 18" forms an obtuse angle at the intersection of the line 22 and the edge 18" (FIG. 2).

The funnel element 26" has an elongate anterior portion 39, which includes the corners 32 and 32' and a posterior portion 40, formed in part by the pair of flaps 34 and 34'. The flaps 34 and 34' may be folded outwardly to facilitate a better fit and increase user comfort, as illustrated in FIG. 3.

When the flaps 34 and 34' are folded along the scored lines 36 and 36', the resulting edges formed along the lines 36 and 36' cooperate with the edges 30 and 30' to form an upper rim 42 which defines an inlet of the funnel element 26". The rim 42 is curved to better conform to the female anatomy. The anterior portion 39 is elongate to allow the user to more easily hold the appliance in place during use. As best seen in FIG. 3, the corners 32 and 32' are rounded, and are not joined together, but rather remain separate to form two tabs for increased comfort and better conformation to the user's body.

Figure 4:
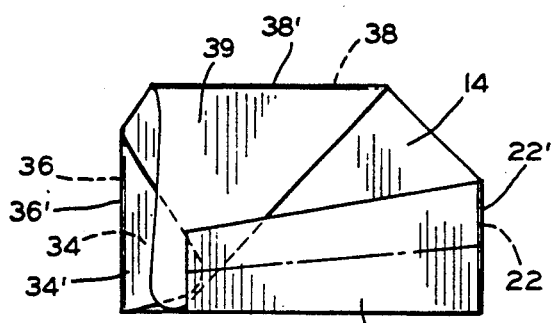
FIG. 4 is a side elevational view of the urinary device shown in FIGS. 2 and 3, illustrating the urinary device in a folded condition for packaging.

The urinary device is packaged and provided in a flat folded condition, with the side walls 14 and 16 in abutting relationship. As illustrated in FIG. 4, both of the flaps 34 and 34' are folded along respective scored lines 36 and 36' to lay flat against the side wall 14. The anterior portion 39 of the funnel element 26" is similarly folded flat along the scored lines 38 and 38', and the tubular element 24" folded flat along the scored lines 22 and 22' to lie adjacent the side wall 14.

To prepare the urinary device for use, the user takes it from its packaging and unfolds the flattened tubular element 24" the anterior portion 39 and the flaps 34 and 34'. With the urinary device thus unfolded, the side walls 14 and 16 may be expanded laterally outwardly from each other by compressing the anterior edge 18" and the posterior edge 12' toward each other.

As best seen in FIG. 3, the tubular element 24" will flex along the longitudinal scored lines 28 and 28' to assume a diamond-shaped cross section. The funnel element 26" will assume a generally funnel shape, with an generally elliptical rim 42' and transitioning to a diamond shaped cross section at its juncture with the tubular element 24".

To use the urinary device, the user positions the device with the rim 42 against her body and about her urethra. The flaps 34 and 34' in the posterior portion 40 may be folded outwardly along the scored lines 36 for increased comfort and better conformation to the user's body. The anterior portion 39 of the funnel element 26" extends upward to the supra-pubic area of the user, where it may be easily held. The user may grasp the tabs formed by the corners 32 and 32' while allowing the tabs to flex outwardly, thereby providing increased comfort and better conformation of the rim 42 to her body.

In use, the funnel element 26" collects the urine voided from the user and directs it into the tubular element 24". The tubular element 24" forms an angle with respect to the longitudinal axis of the funnel element 26", and extends anteriorly with respect to the funnel element 26". The urine is thus directed by the tubular element 24" in an anterior direction. Observing the direction of the tubular element 24", the user may easily direct the stream of urine from the tubular element 24" into a suitable container or receptacle.

In hospitals and medical offices, patients must often provide urine samples for analysis. The urine samples are typically collected in small specimen containers. Females often have difficulty in directing their urine into a specimen container without the use of a funneling device, and may spill urine on the outside of the specimen container, rendering the specimen container unsanitary and unpleasant for the medical personnel to handle during processing. Since the urinary device may be held with one hand and projects anteriorly, a user may hold the device of the present invention with one hand, the specimen container with the other, observe the position of the tubular element 24", and accurately direct the flow of urine into the specimen container. Additionally, the device may easily be formed under sanitary conditions, and provided in a sterile package to meet medical needs.

The urinary device may be packaged in individual packages or a convenient multiple unit package. The size is small enough to permit users to carry the urinary device in a purse or other convenient carrying means.

To facilitate the disposal of the urinary device, it is preferably formed of a biodegradable material. Obviously, the device must be at least temporarily waterproof, but, in order to facilitate its disposal by flushing in a toilet, the device is preferably formed of a material which will break down after sustained exposure to water. Certain types of paper or light cardboard material may suitably be used. Such materials are inexpensive and easily formed, resulting in a low cost of manufacture.

Figure 5:
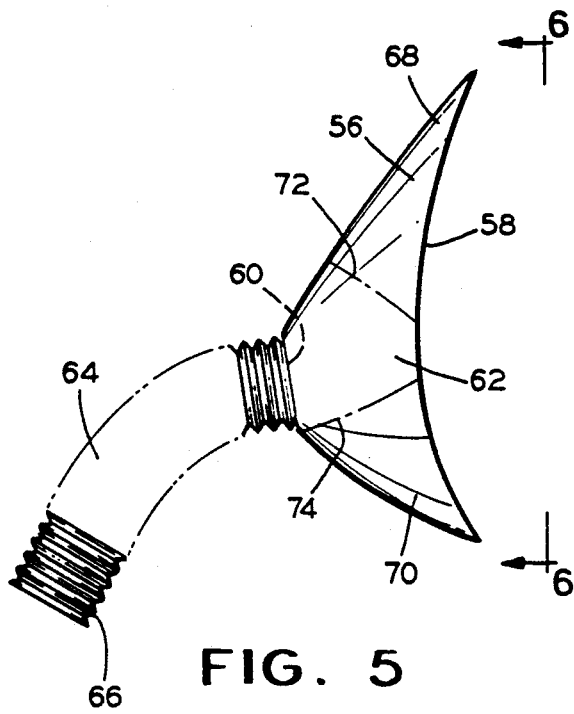
FIG. 5 is a side elevational view of a second embodiment of the present invention in an open and extended position.
Figure 6:
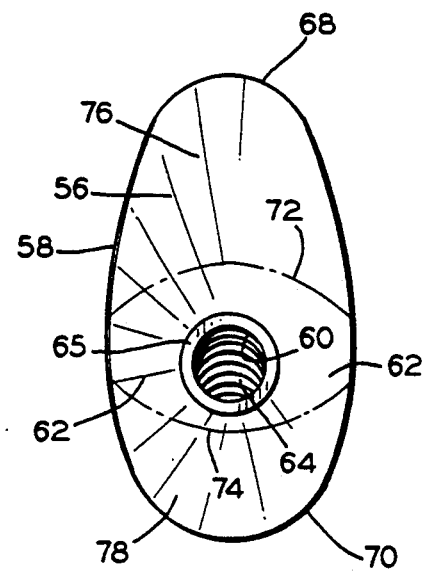
FIG. 6 is a view through the inlet of the urinary device as seen generally along the view line 6—6 of FIG. 5 and showing the device in its open, extended position.

A second embodiment of the urinary device, as illustrated in FIGS. 5 and 6, includes a cup like reservoir 56 with an inlet 58, an outlet 60, and sides 62 that taper from the inlet toward the outlet, and a tubular member 64. The reservoir 56 may be formed by methods well known in the art, preferably from a C-shaped blank (not shown).

One end of the tubular member 64 is provided with a flange 65 (FIG. 6). The flange 65 is adhesively secured or otherwise suitably affixed to the inner surface of the reservoir 56 proximate the outlet 60 so as to form a fluid-tight joint. The tubular member 64 extends through the outlet 60 to project outwardly from the reservoir 56. The use of the flange 65 improves the structural integrity of the urinary device.

The tubular member 64 is formed with circumferential accordion pleats 66 extending the length thereof (as indicated by phantom lines in FIG. 5) by methods well known in the art, in the same manner as flexible paper drinking straws. Such straws are provided with pleats in order to be bendable without collapsing the lumen of the straw.

A front flap 68 is integrally formed on one side of the reservoir 56, and a rear flap 70 is integrally formed on the opposite side. The front flap 68 and the rear flap 70 are flexible along creases 72 and 74, respectively, shown in phantom line in FIGS. 5 and 6.

The flaps 68 and 70 include respective inner surfaces 76 and 78 (FIG. 6). The surfaces 76 and 78 may include a layer of tissue paper or other absorbent material (not shown). This provides a soft touch when the device is positioned for use. The surfaces 76 and 78 may also be used for wiping any excess urine after use.

As in the first embodiment, the urinary device may be constructed of light cardboard, treated paper, or other material which can be folded into the desired configuration and which is temporarily waterproof. The medical applications of the device are again enhanced by convenient and potentially sterile packaging, and the disposable nature of the device.

Figure 7:
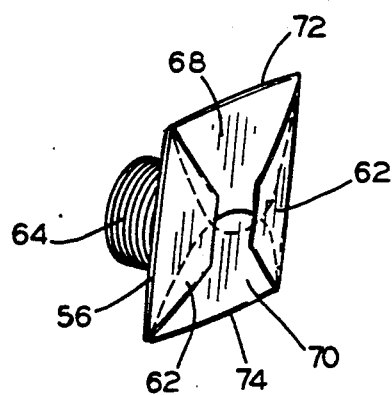
FIG. 7 is a perspective view of the urinary device illustrated in FIGS. 5 and 6 collapsed for packaging.

FIG. 7 shows the urinary device in a compressed and folded condition for packaging, storage, and handling of the device prior to use. To prepare the urinary device for use, the user expands the reservoir 56 by folding the sides 62 and the flaps 68 and 70 to the outside. To expand the tubular member 64 for use, the reservoir 56 is grasped with one hand and the free end of the tubular member 64 is typically pulled outwardly to the desired length and direction with the other hand.

To use the urinary device, a female user positions the inlet 58 about the urethra. The urine from the female may then be voided into the reservoir 56, directed through the outlet 60 into the tubular member 64, and discharged out the open end thereof.

As noted above, the tubular member 64 is provided with accordion pleats 66 along its full length. Consequently, the tubular member 64 is both extensible and flexible, which provides many advantages for users of the device. The flexible tubular member 64 can be bent at any position along the length thereof to discharge the urine in a desired direction, as shown in FIG. 5. When the flexible tubular member 64 is bent at the desired angle, the tubular member 64 will tend to retain such position. The user may thus more easily direct urine in the desired direction, such as into a toilet bowl when using a public restroom, or into a specimen container for urine analysis. Suitably, the tubular member 64 may be provided with a taper to provide a smaller diameter open end which may be more easily inserted into a specimen container.

In accordance with the provision of the patent statutes, the present invention has been described in what is considered to represent its preferred embodiment. However, it should be noted that the invention can be practiced otherwise than as specifically illustrated and described without departing from its spirit or scope.

What is claimed is:

1. A blank for forming a disposable urinary funnel receptacle, comprising:

A. a main body portion formed of a flexible, fluid resistent sheet material, said body portion including,
   (1) a discharge edge;
   (2) a receiving edge spaced from said substantially parallel to said discharge edge;
   (3) a longitudinal scored centerline extending from a midpoint of said discharge edge to a midpoint of said receiving edge, said main body folded along the centerline to divide said body portion into two substantially symmetrical halves, each symmetrical half including;
      (a) a longitudinal edge spaced from said centerline, said longitudinal edge including a first segment extending from said discharge edge, diverging from said centerline at a first angle, and terminating in a second segment, the second segment extending from the termination of the first segment to said receiving edge at a second angle diverging from said centerline, the second angle being greater than the first angle;

(b) said receiving edge including a curved segment extending from the termination of the second segment of said longitudinal edge to said centerline;

(c) a scored transverse fold line extending between an intermediate point on said centerline to the termination of the first segment of said longitudinal edge;

(d) a scored longitudinal flex line located approximately midway between said centerline and the first segment of said longitudinal edge, and extending from said discharge edge to said scored transverse fold line whereby the longitudinal flex line and the first segment of said longitudinal edge both terminate at the transverse fold line;

(e) a scored longitudinal fold line extending from said receiving edge to the second segment of said longitudinal edge; and B. a first foldable tab extending along the first segment and a second foldable tab extending along the second segment of one of said longitudinal edges for attachment along the other of said longitudinal edges in assembling the urinary device.

2. The blank for forming a disposable urinary funnel receptacle defined in claim 1 wherein said receiving edge is curved to conform to the female anatomy whereby said receiving edge is adapted to engage a female body about the urethra when the blank is formed as urinary funnel receptacle.

3. The blank for forming a disposable urinary funnel receptacle defined in claim 1 wherein said receiving edge includes an outwardly curving segment adjacent said centerline, and a second scored transverse fold line extending from the midpoint of said receiving edge at said centerline to said receiving edge.

4. A blank for forming a disposable urinary funnel receptacle, comprising:

A. a main body portion formed of a flexible, fluid resistent sheet material, said body portion including;
   (1) a discharge edge;
   (2) a receiving edge spaced from and substantially parallel to said discharge edge;
   (3) a longitudinal scored centerline extending from a midpoint of said discharge edge to a midpoint of said receiving edge, said main body folded along the centerline to divide said body portion into two substantially symmetrical halves, each symmetrical half including;

(a) a longitudinal edge spaced from said centerline, said longitudinal edge including a first segment extending from said receiving edge, diverging from said centerline at a first angle, and terminating in a second segment, the second segment extending from the termination of the first segment to said receiving edge at a second angle diverging from said centerline, the second angle being greater than the first angle;

(b) said receiving edge including a curved segment extending from the termination of the second segment of said longitudinal edge to said centerline, said receiving provided with an outwardly curving segment adjacent said centerline;

(c) a first scored transverse fold line extending between an intermediate point on said centerline to the termination of the first segment of said longitudinal edge; and (d) a second scored transverse fold line extending from the midpoint of said receiving edge at said centerline to said receiving edge;

(e) a scored longitudinal fold line extending from said receiving edge to the second segment of said longitudinal edge; and (f) a scored longitudinal flex line located approximately midway between said centerline and the first segment of said longitudinal edge, and extending from said discharge edge to said scored transverse fold line whereby the longitudinal flex line and the first segment of said longitudinal edge both terminate at the first transverse fold line; and B. foldable tabs extending along the first segment and the second segment of one of said longitudinal edges for attachment along the other of said longitudinal edges in assembling the urinary device, whereby said body portion may be folded along the longitudinal centerline and said tabs attached to said longitudinal edge of the opposing planar half, the planar halves being flexibly joined along said centerline and said longitudinal edge, and being free of attachment along said discharge edge and said receiving edge such that said blank may be folded along said first transverse fold line, said second transverse fold line, and said longitudinal fold line for storage, and that said blank may be expanded to form an expanded funnel element and tubular element for use as a urinary device by a female in a standing position.

5. The blank for forming a disposable urinary funnel receptacle defined in claim 4 wherein said receiving edge is curved to conform to the female anatomy whereby said receiving edge is adapted to engage a female body about the urethra when the device is used as a urinary funnel receptacle.

* * * * *